United States Patent [19]
Nathel et al.

[11] Patent Number: 5,570,182
[45] Date of Patent: Oct. 29, 1996

[54] METHOD FOR DETECTION OF DENTAL CARIES AND PERIODONTAL DISEASE USING OPTICAL IMAGING

[75] Inventors: Howard Nathel, Albany; John H. Kinney, Danville; Linda L. Otis, San Francisco, all of Calif.

[73] Assignee: Regents of the University of California, Oakland, Calif.

[21] Appl. No.: 250,492

[22] Filed: May 27, 1994

[51] Int. Cl.⁶ .................................................. G01D 9/02
[52] U.S. Cl. .......................................... 356/345; 356/360
[58] Field of Search .................................. 356/345, 359, 356/360, 361

[56] References Cited

U.S. PATENT DOCUMENTS 5,155,363  10/1992  Steinbichler et al. ............... 356/359

FOREIGN PATENT DOCUMENTS 2019930  11/1992  WIPO ................................. 356/345

*Primary Examiner*—Samuel A. Turner
*Attorney, Agent, or Firm*—Daryl S. Grzybicki; Henry P. Sartorio

[57] ABSTRACT

A method for detecting the presence of active and inactive caries in teeth and diagnosing periodontal disease uses non-ionizing radiation with techniques for reducing interference from scattered light. A beam of non-ionizing radiation is divided into sample and reference beams. The region to be examined is illuminated by the sample beam, and reflected or transmitted radiation from the sample is recombined with the reference beam to form an interference pattern on a detector. The length of the reference beam path is adjustable, allowing the operator to select the reflected or transmitted sample photons that recombine with the reference photons. Thus radiation scattered by the dental or periodontal tissue can be prevented from obscuring the interference pattern. A series of interference patterns may be generated and interpreted to locate dental caries and periodontal tissue interfaces.

30 Claims, 6 Drawing Sheets

METHOD FOR DETECTION OF DENTAL CARIES AND PERIODONTAL DISEASE USING OPTICAL IMAGING

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The invention relates to imaging of dental and periodontal tissue. More particularly, the invention relates to a method for detection of caries and periodontal disease by an optical imaging technique that is non-invasive and uses non-ionizing radiation.

2. Description of Related Art

Dental caries, caused primarily by bacterial action on sugars, are a common disease that can be easily treated if detected early. If undetected and untreated, caries may progress through the outer enamel layer of a tooth into the softer dentin so far as to require extraction of the tooth or to cause inflammation of periodontal tissue surrounding the tooth. The standard methods for detecting caries in teeth are by visual inspection or by the use dental x-rays. Both methods are unreliable for the detection of small caries (<1 mm) or caries between teeth. In addition, dental x-rays subject the patient to ionizing radiation, a known mutagen.

Non-ionizing radiation has long been used for imaging the internal structures of soft tissue, and has shown promise in such applications as mammography, neonatal brain scanning and imaging of some tumors. Generally, however, it is unsatisfactory for tissue imaging because scattering of the lower-energy non-ionizing radiation by the tissue severely compromises the resolution of the image. Although resolution of optical images may be improved by the use of polarizing filters or phase conjugated mirrors, or by collimation of the incident and transmitted beams to reduce interference from scattered radiation, x-ray images still produce superior resolution. Optical imaging with non-ionizing radiation requires sophisticated techniques such as photon time-of-flight range gating to achieve image resolution comparable to x-ray techniques.

Several imaging techniques for hard tissue such as teeth use non-ionizing radiation. Caries may be detected using visible luminescence, based on the discovery that in certain regions of the visible spectrum the intensity of the luminescence for carious and noncarious dental tissue is nearly the same, while in other regions the luminescence intensity increases substantially in the presence of caries. The method involves illuminating a tooth at two wavelengths, one where the intensity is similar, and another where the intensity increases in the presence of caries, then comparing the intensity of the visible luminescent radiation at the two wavelengths. Some preliminary attempts have been made to image teeth with transillumination techniques using non-ionizing radiation, with collimation of the incident and transmitted beams to reduce interference from scattered light. The method presently requires 1.5 hours to image one tooth with 1.5 mm$^2$ resolution, and so is unsuitable for clinical use.

A need exists for a new technique for detecting the presence of carious tissue in teeth that eliminates the exposure to ionizing radiation, yet offers the resolution and rapid imaging capability of x-ray techniques. In a portion of the visible and near infrared spectrum, light can be transmitted through or reflected from internal structures in hard tissue, such as a tooth. Also, in the wavelength region between 500 nm and 1400 nm carious dental tissue is much more strongly absorbing than healthy dental tissue, and conversely that optical radiation is more strongly transmitted through or reflected from healthy dental tissue. The present invention uses these differential transmission, reflection, and absorption characteristics of healthy and carious dental tissue to create a shadowgraph of structures, such as caries, in a tooth, using nonionizing radiation. The present invention also improves the spatial resolution of an imaging system for detection of caries. Resolution is achieved by photon time-of-flight range-gating techniques coupled with optical heterodyne detection. These techniques are well-known and widely used in applications that require fast imaging and superior image resolution. The present invention also offers an image acquisition time that will allow its use in a clinical setting.

Periodontal disease is the major cause of tooth loss. Plaque is formed by bacterial action on food, and causes inflammation of the epithelial and connective tissue around a tooth. Untreated, such an inflammation can result in loss of the connective tissue and bone that anchor the tooth, and ultimately loss of the tooth itself. Present methods of diagnosing and monitoring a periodontal disease such as gingivitis (inflammation of the gum) rely primarily on the use of a mechanical probe to determine the epithelial attachment point and the depth of the periodontal pocket. Several types of mechanical probes are in use, including a probe with a calibrated flexible tip, allowing the examiner to probe the periodontal pocket without penetrating the wall of the pocket and to follow the contours of the dental tissue. Calibrations on the probe show the depth that the probe penetrates between the tooth and gum, and indicate the progress of periodontal disease. Another periodontal probe instrument includes a pressure sensor that activates a signal processing apparatus to simultaneously measure probe pressure, periodontal pocket depth, and periodontal attachment point.

An ultrasound probe has been revealed as a noninvasive method of recording the depth of the periodontal pocket between a tooth and a gum by comparing the delay time of ultrasonic pulses reflected at the top surface of the gum and pulses reflected at the bone surface below the periodontal pocket. Ultrasound, however, is not suitable for early detection of gingivitis because the technique measures the alveolar bone level rather than the point of epithelial tissue attachment. Gingivitis in the early stages is characterized by changes in the epithelial attachment level and the formation of a pocket between the tooth and epithelium, rather than loss of bone.

The present invention fills a need for an accurate method of diagnosing and monitoring the periodontal disease known as gingivitis. The methods currently in use that depend on a measure of probe penetration have several significant sources of error, because probe penetration may vary with insertion force, tissue inflammation, and diameter of the probe tip. In the present invention, detection and monitoring of gingivitis is accomplished by measuring the reflection of optical radiation from dental and periodontal tissue boundaries. Light is both reflected from and transmitted through the interface between tissues with even slightly different indices of refraction. Light reflected from an interface can be detected and, with interferometry, can be used to accurately determine the location of the tissue boundary. The present invention allows precise measurements to be taken of the gap between the epithelial tissue and tooth, the depth of the periodontal pocket, the point of epithelial attachment, and the position of the cemento-enamel junction. With these measurements, a two- or three-dimensional optical map may be created of the periodontal pocket, permitting an earlier and more accurate diagnosis of gingivitis. Besides eliminating measurement errors caused by variability of examiner probing methods, diagnosis and monitoring using the present invention is more comfortable for the patient. In addition, the optical images or maps produced may be maintained with patient records, and a series of optical images taken over time may be compared to monitor the progress of gingivitis and assess treatment methods.

SUMMARY OF THE INVENTION

It is an object of the invention to provide a method of imaging dental tissue that does not involve exposure to ionizing radiation.

It is a further object of the invention to provide a method for detecting carious dental tissue that surpasses the detection capability of current methods.

It is another object of the invention to provide a non-invasive method of diagnosing and monitoring the periodontal disease known as gingivitis.

It is also an object of the invention to provide an optical probe to reproducibly and accurately characterize the anatomical morphology of the periodontal pocket adjacent to a tooth.

It is further an object of the invention to provide a method for characterizing the morphology of a periodontal pocket that is more complete, reproducible, and accurate than methods presently in use.

The present invention is a method of optical imaging that may be used both for the detection of caries and for the diagnosis and monitoring of gingivitis. The invention uses optical radiation in the wavelength region between 500 nm and 1400 nm, where carious dental tissue is much more strongly absorbing than healthy tissue, so that transmitted or reflected optical radiation can be used to create a shadowgram of structures within the dental tissue. The same wavelength region may be used for the detection and location of tissue boundaries by which the invention is used to diagnose and monitor the progress and treatment of gingivitis.

Because non-ionizing radiation that penetrates tissue will be subject to significant scattering inside the tissue, techniques to reduce interference from scattered radiation are central to the invention. Image fidelity is maintained by discriminating between photons that undergo minimal or no scattering in the dental or periodontal tissue, and photons that are highly scattered. Photons that pass straight through tissue traverse a shorter pathlength, and retain their coherence, compared to photons that are scattered within the tissue. Thus unscattered photons can be separated from scattered photons using time-of-flight range gating techniques (for a highly coherent, pulsed source of optical radiation) or coherence techniques with optical heterodyne detection (for a continuous-wave low coherence, or broadband, source).

Various embodiments of the invention allow two- or three-dimensional imaging of dental and periodontal tissue using transmitted or reflected optical radiation from a highly coherent pulsed source or from a continuous wave low-coherence source. The particulars of the application will determine the most suitable optics and optical radiation source.

DETAILED DESCRIPTION OF THE INVENTION

Figure 1A:
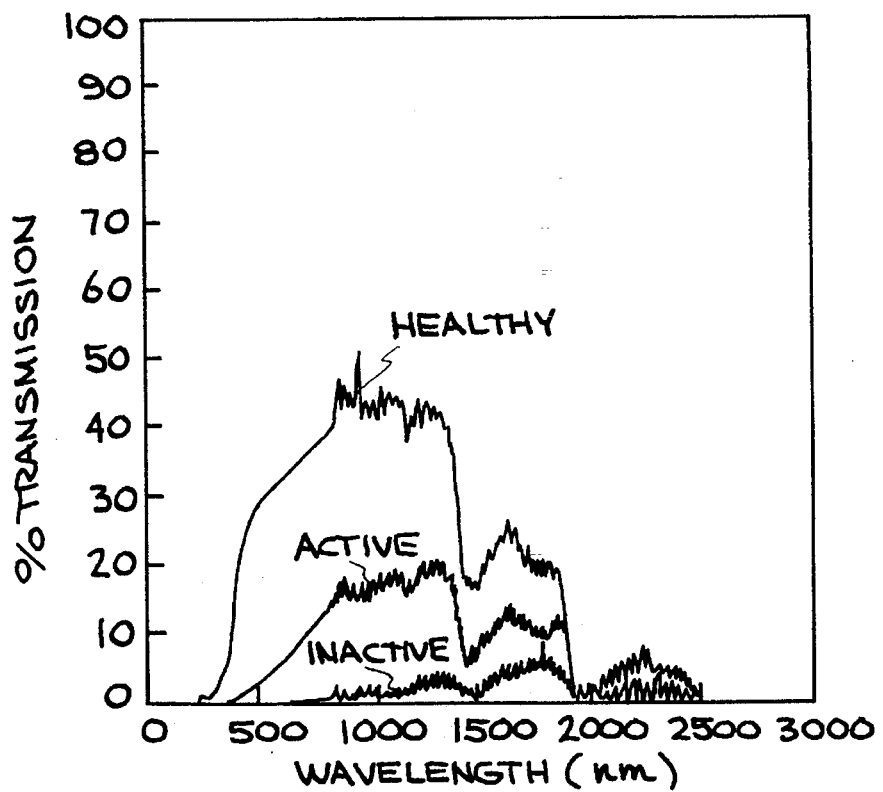
FIGS. 1A–C show respectively the transmission, reflection, and absorption spectra of healthy and carious dental tissue in the wavelength region 300 nm to 2500 nm.
Figure 1B:
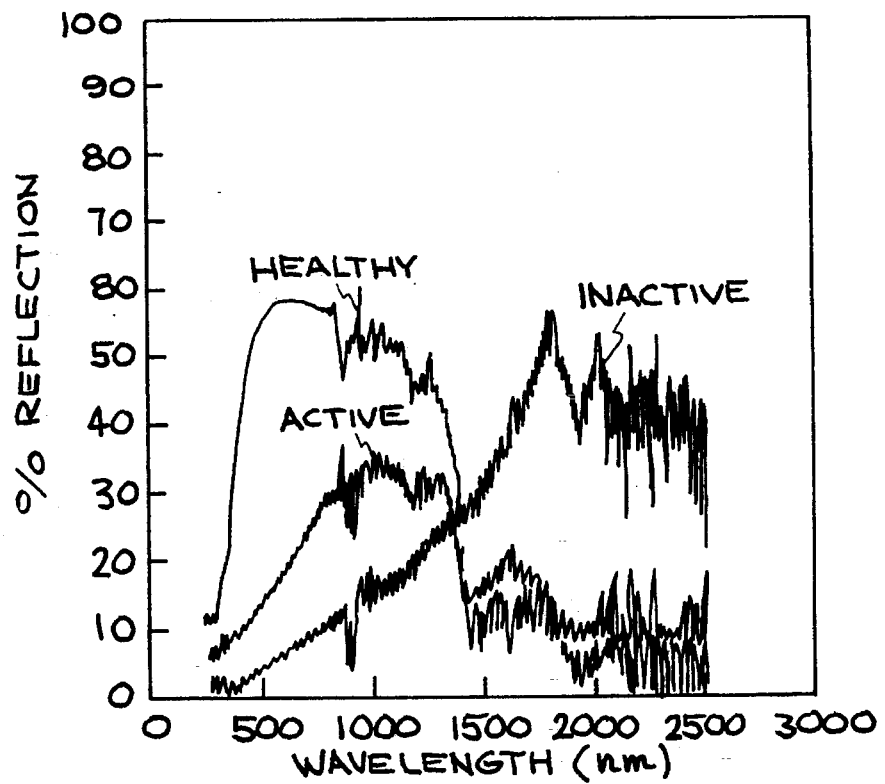
Figure 1C:
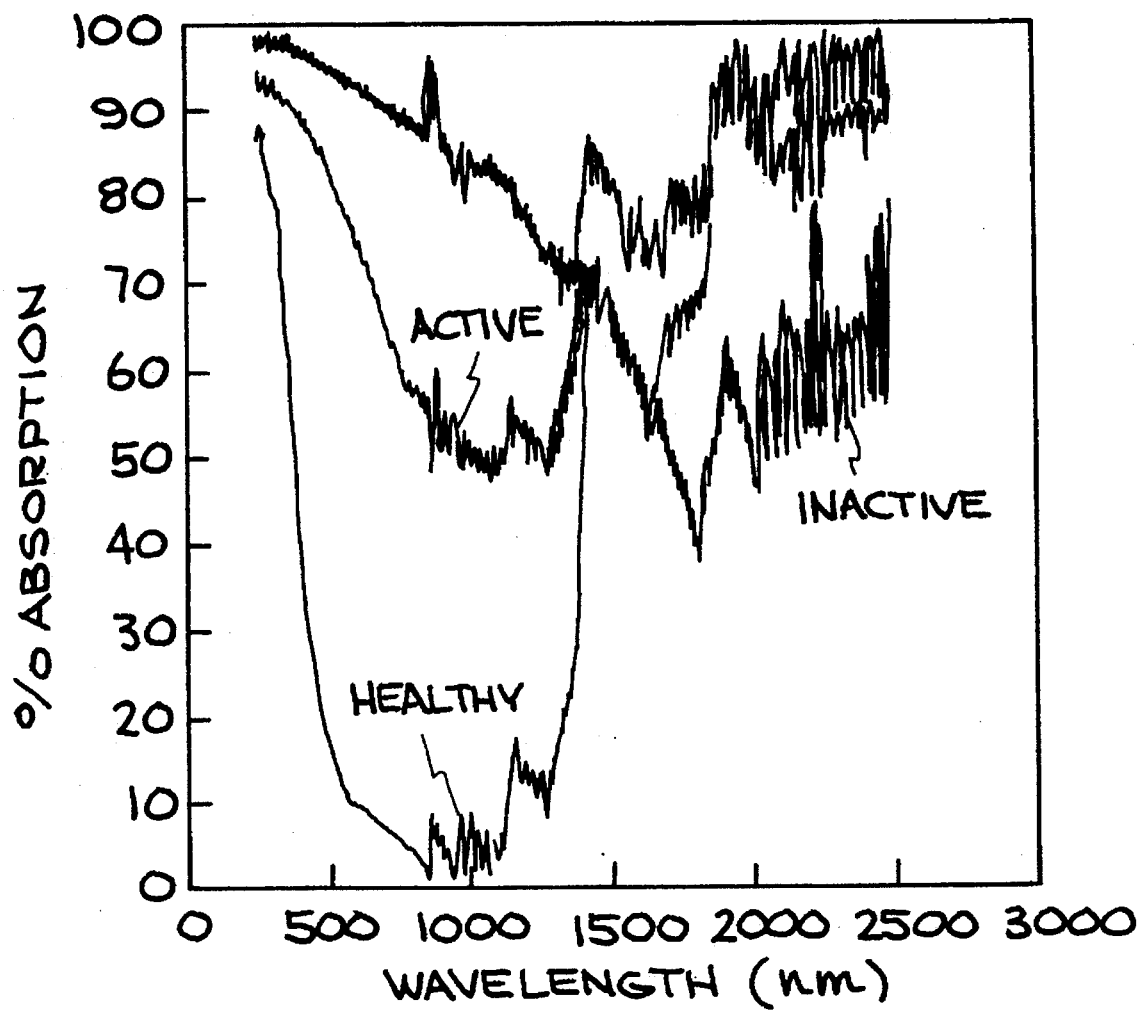

This invention makes use of the difference in absorption spectra between carious and healthy dental tissue in the wavelength region 500 nm to 1400 nm, and of the differential indices of refraction of various dental and periodontal tissues. FIG. 1A is a comparison of the transmission spectra of healthy and carious dental tissue, showing that healthy tissue is much more strongly transmitting than active and inactive carious tissue, especially in the near infrared region between 800 nm and 1200 nm. FIG. 1B shows that healthy dental tissue is more strongly reflecting than carious tissue; again this is most apparent in 800 nm to 1200 nm region. FIG. 1C compares absorption spectra of healthy and carious tissue, and indicates that carious tissue is more strongly absorbing in the near infrared. The differential absorption in this region between healthy and carious tissue may be used to generate a shadowgram of a tooth, showing the location of active and inactive carious tissue. Light passing through carious tissue will be more strongly absorbed, so that changes in the intensity of a reflected or transmitted light beam can be detected on a receiver, and the data collected to map the location of caries in a tooth.

The wavelength region around 800 nm is particularly interesting for several reasons. From the spectra in FIGS. 1A–C it is clear that there is significant contrast between healthy and carious tissue in that region. In addition, there is a wide variety of light sources available in that region, and standard photodetectors have a high quantum efficiency in that wavelength region.

Figure 2:
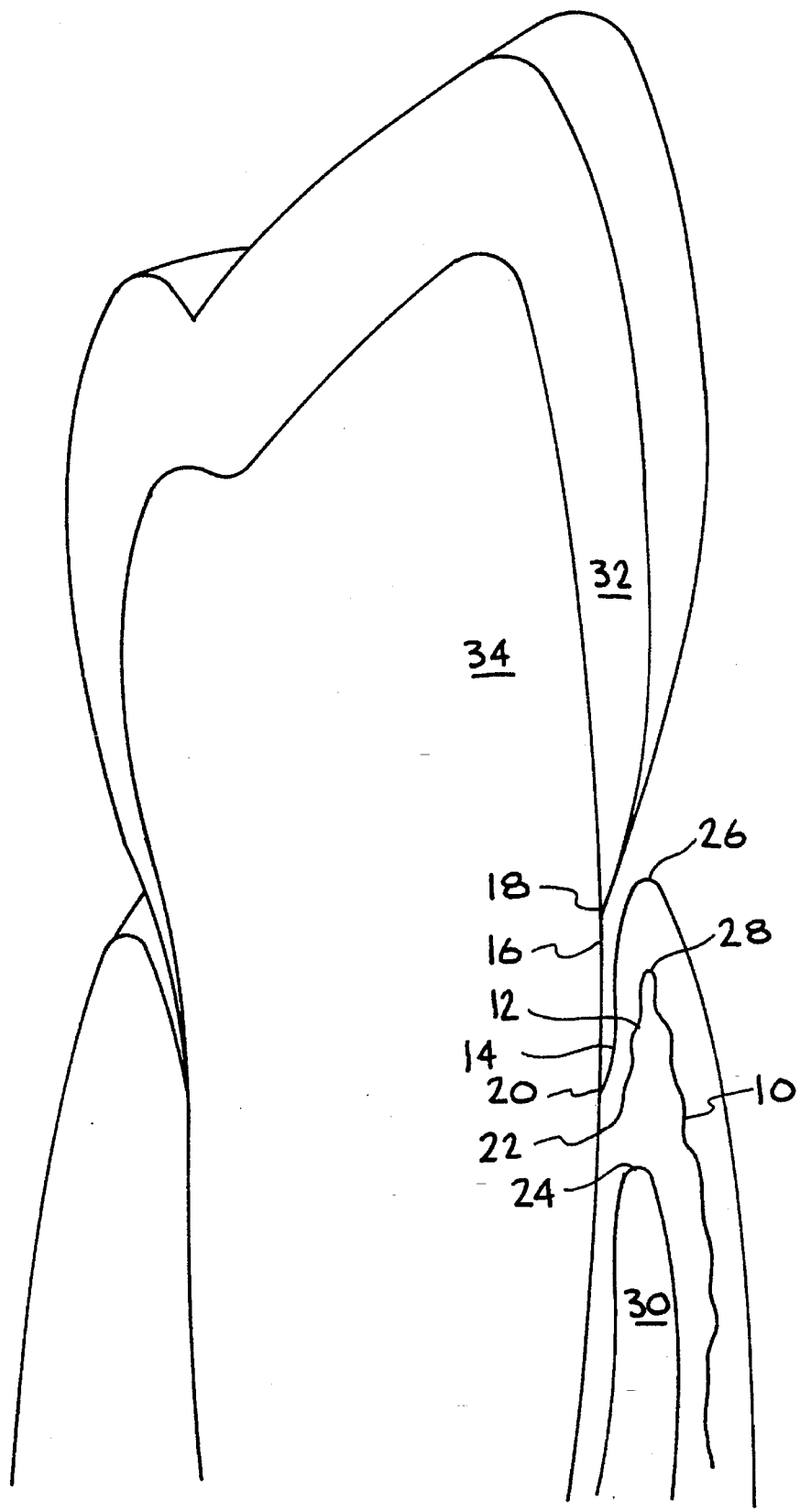
FIG. 2 shows a detailed picture of the periodontal pocket and tissue interfaces that can be characterized and mapped by the invention.

FIG. 2 shows the interfaces that are measured to diagnose and monitor the progress of gingivitis, a periodontal disease characterized by inflammation of the epithelial tissue 26 and connective tissue 28, and eventually by loss of connective and epithelial tissue attachment and alveolar bone 30. The optical imaging technique described in the preferred embodiment may be used to develop a map of the periodontal pocket, defined as the gap between the epithelium surface 14 and the tooth surface 16, that develops with the progression of gingivitis. A critically important measurement in the diagnosis of gingivitis is the attachment level, defined clinically as the distance from the cemento-enamel junction 18, where the surface of the tooth changes from enamel 32 to dentin 34, to the epithelial attachment point 20. Accurate measurement of the attachment level, and any changes in the attachment level over time, are integral to establishing a diagnosis of gingivitis and monitoring the progress and treatment of the disease. The imaging technique in the preferred embodiment may be used to precisely locate epithelium/connective tissue interfaces 10 and 12, epithelium surface 14 and tooth surface 16, cemento-enamel junction 18, epithelial attachment point 20, connective tissue attachment point 22, and alveolar bone level 24. A series of these measurements may be taken to determine the attachment levels and the bone level as a function of location. A three-dimensional optical map may be produced that will provide rapid, consistent, and reproducible documentation of the pocket and periodontal morphology.

In the preferred embodiment of this invention, interference from scattered photons is greatly reduced by employing optical coherence interferometry (optical time domain reflectometry in the time domain or optical coherence reflectometry in the frequency domain). A beam of photons from a source of non-ionizing radiation is split into sample and reference beams. The sample beam is focused onto a surface of the sample to be imaged, and the beam of coherent reflected photons is collected from the sample. Simultaneously the reference beam is directed through a reference path having a variable length. The length of the reference path is varied by impinging the reference beam onto a reflecting mirror that is movable along the axis of the reference beam. The reference beam is reflected by the mirror toward a means for recombining the reflected sample beam and the reference beam to form an interference pattern. The pathlength of the reference beam is adjusted so that only coherent reflected sample photons contribute to the interference pattern formed by recombining the reference and sample beams. The interferogram is collected on a photodetector, preferably with optical heterodyne detection to enhance sensitivity (signal to noise ratio), and digitally reconstructed with the aid of a computer.

Optical heterodyne detection is used in some embodiments of the invention to eliminate the background interference arising from the photons diffusely scattered by the sample tissue. Optical heterodyne detection may be accomplished by placing a modulation device, such as a piezoelectric transducer or an acousto-optic modulator, in the sample beam, or by producing a Doppler shift in the reference beam. Point-by-point scanning to produce a cross-sectional image, however, requires modulation of the sample beam rather than the reference beam. With modulation of either the sample beam or reference beam and demodulation with either an envelope detector or a lock-in amplifier, it is possible to achieve sensitivity approaching the shot noise limit, or quantum limit. Optical heterodyne detection is an established method of optimizing the sensitivity of an optical system, and is discussed in more detail in several publications such as Gilgen et al., "Submillimeter optical reflectivity", J. Lightwave Technol. 7(8):1225–1233 (1989), and Beaud et al., "Optical reflectometry with micrometer resolution for the investigation of integrated optical devices", IEEE J. Quantum Electron., 25(4):755–759 (1989).

Figure 3:
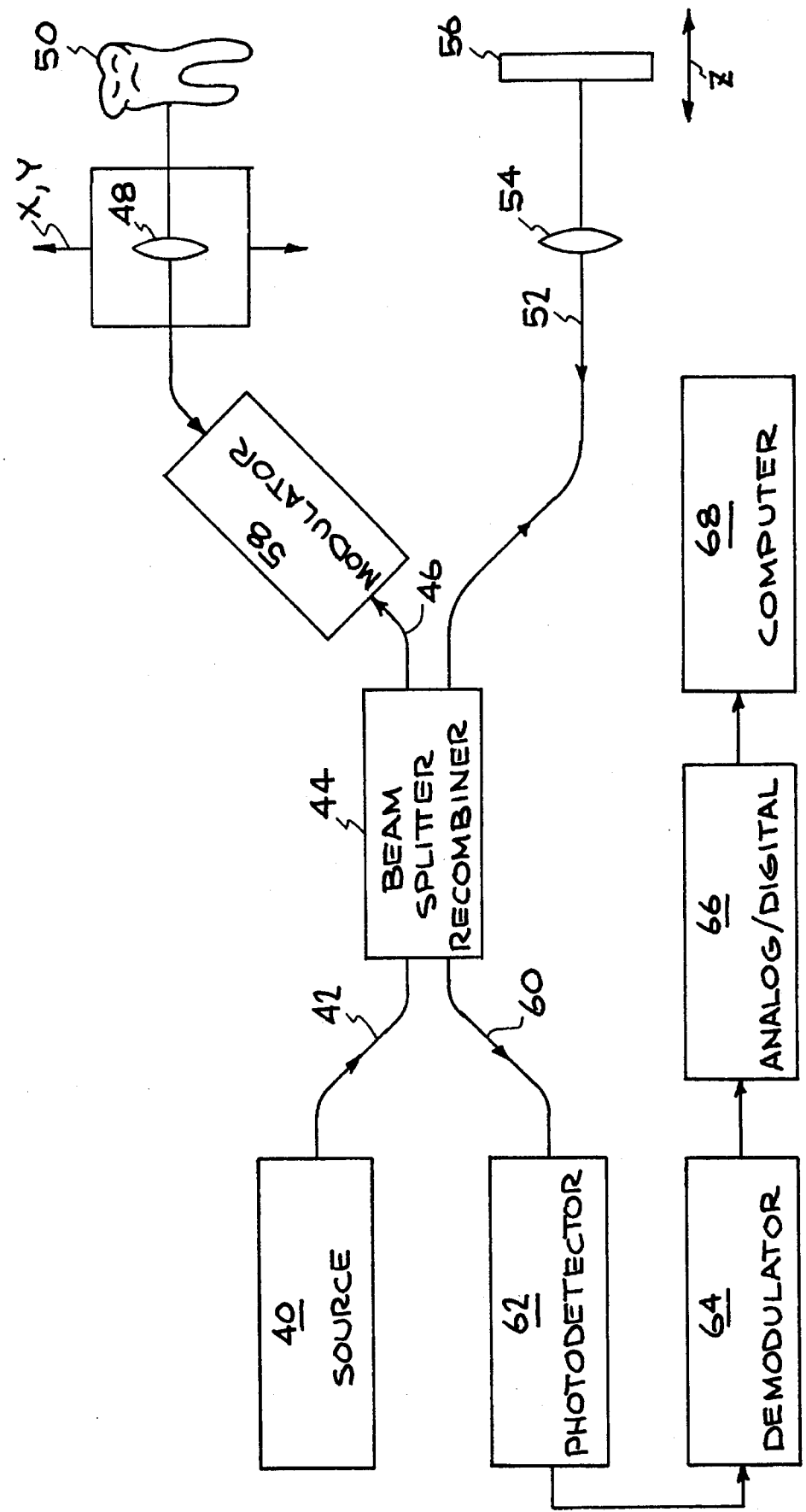
FIG. 3 is a block diagram of a preferred embodiment of the invention.

The principal functional blocks of the preferred embodiment are shown in FIG. 3. Light from an optical source 40 is directed by single mode fiber 42 through a beam splitter/recombiner 44, where it is split into an incident sample beam and an incident reference beam. The incident sample beam is directed by single mode fiber 46 through focusing lens 48 onto a sample 50, and the incident reference beam is directed by single mode fiber 52 through focusing lens 54 onto a reference mirror 56.

For detection of caries in teeth, the sample 50 is the tooth to be imaged. The incident sample beam is directed onto a surface of the tooth 50 and a reflected sample beam, reflected from the dental tissue of the sample, is collected by focusing lens 48. For periodontal applications, the incident sample beam is directed onto the side surface of the epithelial tissue adjacent to a tooth, and the beam reflected from the dental and periodontal tissue interfaces is collected by focusing lens 48.

The reflected sample beam, after collection, is directed back to the beam splitter/recombiner 44 by single mode fiber 46. A modulating device 58 provides the phase modulation for optical heterodyne detection where a low coherence source of optical radiation is used.

Simultaneously with the direction of the incident sample beam onto the sample, the incident reference beam is directed by single mode fiber 52 through focusing lens 54 onto the reference mirror 56. The reflected reference beam is collected on focusing lens 54 and directed back to the beam splitter/recombiner 44 by single mode fiber 52.

The reflected sample beam and reflected reference beam are combined at the beam splitter/recombiner 44, and the resulting interference pattern is directed by single mode fiber 60 onto a photodetector 62. The photodetector output is passed through the demodulation electronics 64 (if optical heterodyne detection is used to reduce interference from scattered photons) and an analog-to-digital converter 66, and may be stored on a computer 68 for analysis and display.

In the preferred embodiment, focusing lens 48 is movable in the x,y plane to allow either one-dimensional or rapid-scan, two-dimensional imaging. One-dimensional vertical scanning would be acceptable for a quick characterization of the periodontal pocket; two-dimensional imaging would be required for detection of caries, and for more comprehensive mapping of the periodontal pocket morphology for the diagnosis and monitoring of gingivitis. The reference mirror 56 is movable in the z direction. This allows the pathlength of the reference beam to be adjusted to produce an interference pattern when combined with optical radiation reflected from the desired depth within the sample. The reference mirror 56 may be vibrated in the z-direction to produce the Doppler shift for optical heterodyne detection if the sample beam is not modulated using the modulator 58.

The source of optical radiation in the preferred embodiment is a continuous wave low coherence, or broadband, source. Preferred low-coherence sources include superluminescent diodes, diode-pumped solid state crystal sources, and diode-pumped rare earth-doped fiber sources. Image resolution is enhanced by optical heterodyne detection combined with frequency domain interferometry. In frequency domain interferometry, an interference pattern is formed only when the sample and reference pathlengths are equal to within the source coherence length, which is inversely proportional to the source bandwidth. Photons in the sample beam that are scattered within the tissue are asynchronous with the photons in the reference beam, and therefore do not contribute to the interference pattern formed by combining the reflected reference beam and the reflected sample beam.

Detection of caries by means of the preferred embodiment involves focusing the sample beam on the side surface of the tooth to be imaged, and collecting photons reflected from dental tissue at various depths within the tooth. The length of the reference path determines the depth from which the reflected sample photons recombine with reference photons to produce an interference pattern. In this way a two- or three-dimensional image of the structures within a tooth may be obtained by scanning the sample beam over the surface of a tooth and collecting reflected sample photons from various depths within the tooth.

Periodontal diagnosis using the preferred embodiment involves scanning the sample beam down the side surface of a tooth and gum, and determining the precise location of various tissue interfaces. The pathlength of photons reflected from each tissue boundary can be precisely determined by adjusting the pathlength of the reference beam to form interference patterns with the unscattered sample photons reflected from the interfaces. The difference in the path lengths of unscattered photons reflected from the various interfaces can be used to determine the epithelial and connective tissue attachment points, location of the cemento-enamel junction, depth of the periodontal pocket, and alveolar bone level. The imaging results may be compared with standard medical criteria to establish a diagnosis of gingivitis.

The optical source for the preferred embodiment may also be a highly coherent source with pulsing means causing the source to emit pulses of $10^{-10}$ to $10^{-14}$ sec, although a system using such a source might be too expensive and cumbersome for some clinical applications. Suitable highly coherent sources include mode-locked diode lasers, diode-pumped mode-locked solid-state crystal sources, and diode-pumped mode-locked rare earth-doped fiber laser sources. With a coherent source, time domain interferometry is used to reduce interference from scattered photons. The reference and sample beams are synchronized by adjusting the position of the reflecting mirror so that the maximum number of coherent reflected sample photons contribute to the interference pattern formed by recombining the reference beam with the reflected sample beam. In practice the reflected sample beam will consist of scattered and unscattered photons; the photons that are scattered by the dental or periodontal tissue have a longer path length, and so are not synchronized with the reference beam and do not contribute to the formation of an interference pattern. With a pulsed source, the ultimate resolution of the optical imaging system is related to the pulse width; millimeter or submillimeter resolution will require a source pulse of several picoseconds or less.

Detection of caries by two- and three-dimensional imaging of structures in teeth is also possible using this invention. A two-dimensional shadowgram may be formed by directing a beam of the appropriate cross section onto the side of a tooth, recombining the reference beam with photons reflected from the dental tissue, collecting on a photodetector array the interference pattern formed by the recombined beams, and reconstructing the image with an analog-to-digital converter and a computer. The shadowgram formed by the recombined beams may also be collected on photographic film for visual analysis. Three-dimensional depth information is obtained by scanning the reference mirror back and forth in the direction of propagation of the reference beam to record a series of two-dimensional shadowgrams of tooth structure at various depths within the tooth. Photons reflected from various depths within the tooth will recombine to form an interferogram only with a reference beam that is within the coherence length of the source (for a broadband source) or with a synchronized reference beam (for a coherent source). A three-dimensional image of the tooth may be generated by reconstruction and analysis of the two-dimensional shadowgrams.

Similarly, a two- or three-dimensional map of periodontal pocket and tissue morphology may be generated. A series of two-dimensional shadowgrams may be formed by recombining the photons in the reference beam with sample photons reflected from periodontal and dental tissue interfaces at various depths within the area of interest, and three-dimensional depth information obtained by computer analysis of the two-dimensional shadowgrams.

Figure 4:
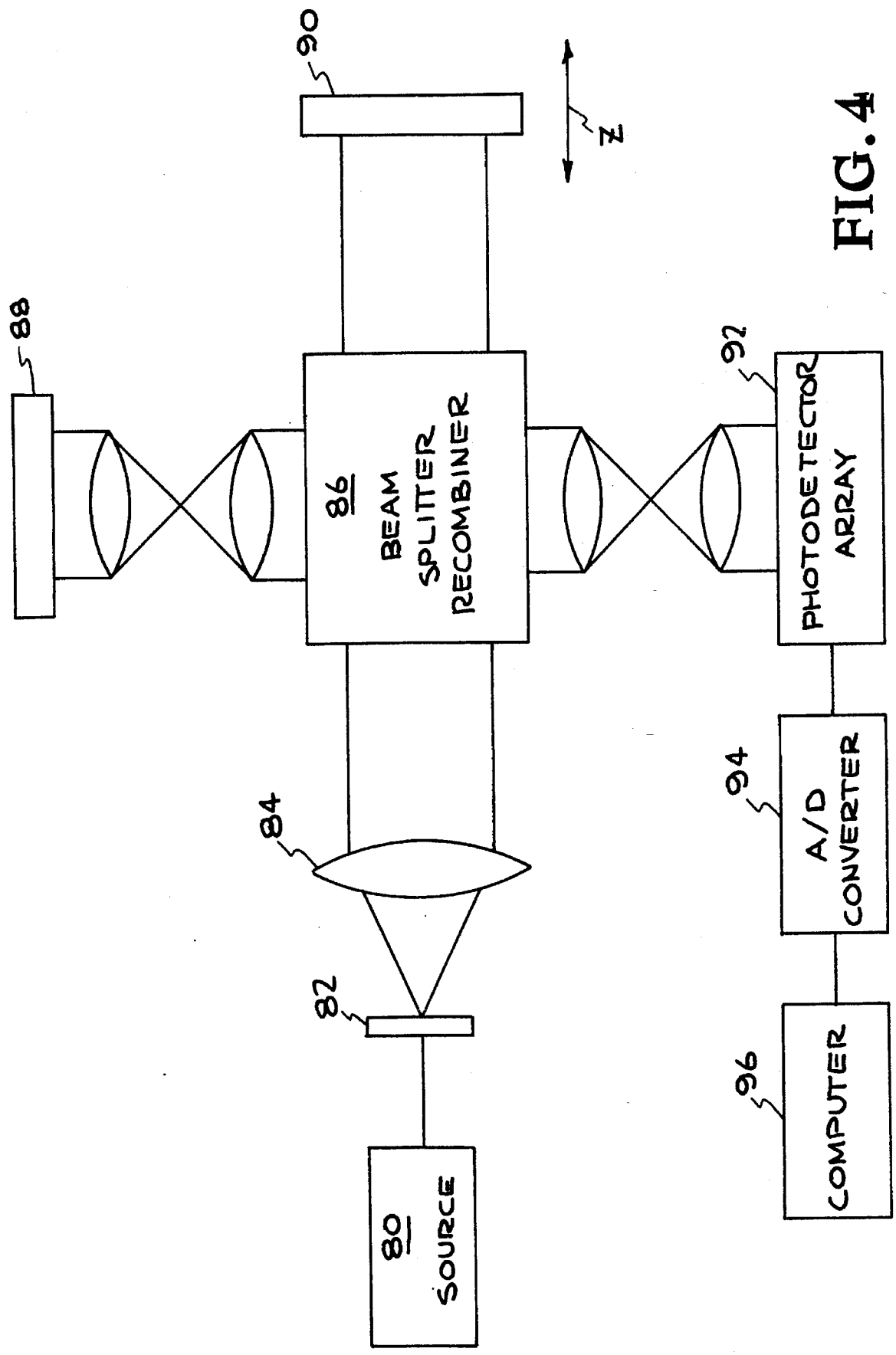
FIG. 4 is a block diagram of an embodiment for generating a two-dimensional or three-dimensional shadowgram using reflected optical radiation.

FIG. 4 shows a block diagram of the optics used to generate a shadowgram of a tooth with reflected optical radiation. Light from an optical source 80 is directed through a spatial filter 82 and a magnifying telescope 84 to a beam splitter/recombiner 86, where the source beam is split into an incident sample beam and an incident reference beam. The incident sample beam is reflected by the beam splitter/recombiner 86 through suitable optics onto a tooth 88, and the reflected sample beam is collected on the beam splitter/recombiner 86. Simultaneously, the incident reference beam is transmitted through the beam splitter-recombiner 86 onto a reference mirror 90, and the reflected reference beam is collected on the beam splitter/recombiner 86. The reflected sample beam and the reflected reference beam are combined and directed through suitable optics onto a photodetector array 92, and the signal from the photodetector array 92 may be reconstructed, stored, and analyzed using an analog-to-digital converter 94 and a computer 96. Alternatively, the shadowgram formed by the recombined beams may be collected on photographic film and visually inspected to detect carious tissue.

The reference mirror is movable in the z direction to allow an image to be created from optical radiation reflected from the desired depth within the tooth. The reference mirror may be scanned in the z-direction while collecting a series of two-dimensional images. The series of images may be reconstructed to produce a three-dimensional image of the tooth.

Dental caries may also be detected by producing a two-dimensional interferogram or shadowgram from optical radiation transmitted through dental tissue, using Mach-Zehnder interferometry. Optical radiation from a broadband source or a highly coherent pulsed source is split into sample and reference beams. The sample beam is directed onto a side surface of the tooth to be imaged, and the beam of photons transmitted through the tooth is collected on the opposite side of the tooth. Simultaneously the reference beam is directed through a reference path having a variable length. The length of the reference path is adjusted by directing the reference beam onto a reflecting mirror that is movable along the axis of propagation of the reference beam. The reflecting mirror directs the reference beam toward a means for recombining the sample and reference beams. To obtain a shadowgram from transmitted radiation, the length of the reference path is adjustable to duplicate the path length of unscattered sample photons through the sample tissue.

Figure 5:
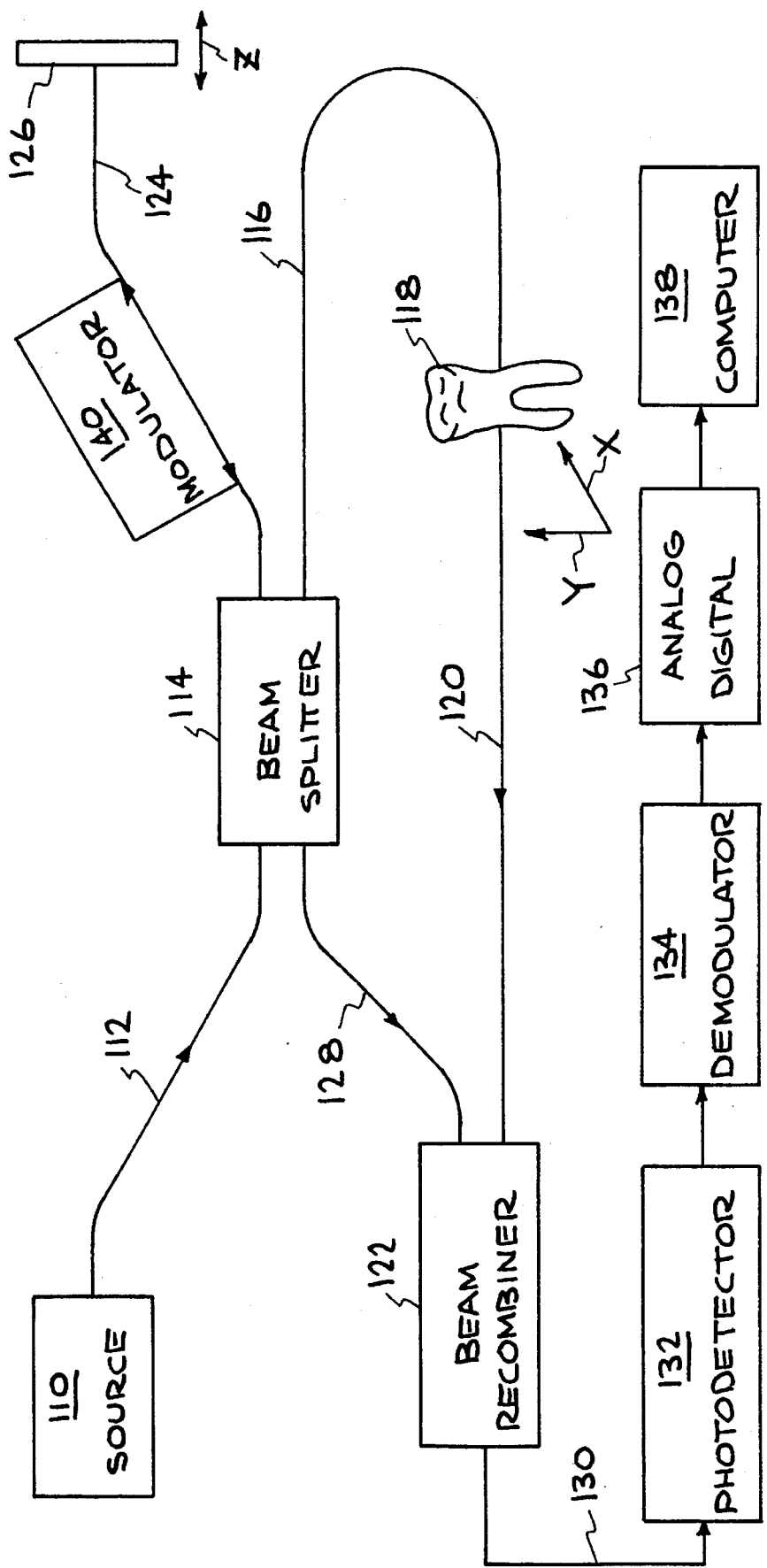
FIG. 5 is a block diagram of an embodiment of the invention for detecting caries by generating an interference pattern from transmitted optical radiation.

FIG. 5 illustrates an embodiment of the invention for point-by-point imaging of dental tissue using transmitted radiation. Light from the optical source 110 is directed by single mode fiber 112 through a beam splitter 114, where it is split into an incident sample beam and an incident reference beam. The incident sample beam is directed by single-mode fiber 116 onto the tooth 118. The transmitted sample beam is directed by single mode fiber 120 to a beam recombiner 122. Simultaneously, the incident reference beam is directed by single mode fiber 124 onto a reference mirror 126, and the reflected reference beam is directed by single mode fiber 124 back through the beam splitter 114. Single mode fiber 128 directs the reflected reference beam to the beam recombiner 122. The recombined beam is directed by single mode fiber 130 onto a photodetector 132. The signal from the photodetector 132 is passed though the demodulation electronics 134 (if optical heterodyne detection is used to enhance the resolution of the image) and reconstructed using an analog-to-digital converter 136 and a computer 138. In transmission mode, the phase modulation for optical heterodyne detection is accomplished by placing the modulating device 140 in the path of the reference beam rather than the sample beam. Optical heterodyne detection is discussed in more detail in connection with the preferred embodiment of the invention.

Single mode fiber 116 directing the sample beam onto the tooth 118 is movable in the x,y plane to allow two-dimensional imaging of the tooth by recording a series of interferograms while scanning the sample beam over the tooth. A two-dimensional shadowgram of structures with a tooth may also be generated using spatial filters and lenses rather than fiber optics (as with two-dimensional imaging in reflection mode). The interference pattern formed by recombining the transmitted sample beam with the reference beam is collected on photographic film for visual observation or on a photodetector array for reconstruction and analysis.

Changes and modifications in the specifically described embodiments can be carried out without departing from the scope of the invention which is intended to be limited only by the scope of the appended claims.

We claim:

1. A method for characterizing dental caries and periodontal disease in dental or periodontal tissue using optical imaging, comprising:

directing non-ionizing radiation of a selected wavelength onto a surface of the dental or periodontal tissue, wherein the wavelength simultaneously maximizes the differential absorption/reflection between carious and healthy dental tissue and the number of photons reflected by the dental tissue, collecting photons reflected by internal structures or interfaces of the tissue, discriminating between photons that are unscattered by the dental or periodontal tissue, and photons that are scattered by the tissue, based on the coherence of the reflected photons, selecting photons that are unscattered by the dental or periodontal tissue, interpreting the distribution of the selected photons to determine the characteristics of the dental or periodontal tissue.

2. A method as described in claim 1, wherein the wavelength of the non-ionizing radiation is in the wavelength region 500 nm to 1400 nm.

3. A method as described in claim 1, wherein the reflected photons are collected on an optical receiver to form an image.

4. A method as described in claim 3, wherein the optical receiver is a photodetector, photodetector array, or photographic film.

5. A method as described in claim 1, wherein the non-ionizing radiation is generated by a source selected from the group consisting of continuous wave low coherence sources and highly coherent sources.

6. A method as described in claim 5, wherein the source is a continuous wave low coherence source selected from the group consisting of superluminescent diodes, diode-pumped solid state crystal sources, and diode-pumped rare earth-doped fiber sources.

7. A method as described in claim 6, wherein the discrimination between scattered and unscattered photons is accomplished by:

splitting an incident beam of non-ionizing radiation into an incident sample beam and a reference beam, focusing the incident sample beam onto one side of the tissue to be imaged, collecting photons reflected from the internal structures or interfaces of the tissue, passing the reference beam through a reference path having a path length which is adjustable to duplicate in the reference path the coherence length of photons in the incident sample beam, recombining the reference beam and collected photons to form an interference pattern.

8. A method as described in claim 7, wherein the interpretation is accomplished by digitally reconstructing the interference pattern.

9. A method as described in claim 7, further comprising scanning the sample beam over the surface of the tissue to be characterized to produce a series of interference patterns.

10. A method as described in claim 5, wherein the source is a highly coherent source selected from the group consisting of mode-locked diode lasers, diode-pumped mode-locked solid-state laser crystal sources, and diode-pumped mode-locked rare earth-doped fiber laser sources.

11. A method as described in claim 10, further comprising pulsing the source to emit pulses of non-ionizing radiation of the selected wavelength of pulse length $10^{-10}$ to $10^{-14}$ seconds.

12. A method as described in claim 11, wherein the discrimination between scattered and unscattered photons is accomplished by:

splitting the incident beam of non-ionizing radiation into an incident sample beam and a reference beam, focusing the incident sample beam on one side of the tissue to be imaged, collecting photons reflected from internal structures or interfaces of the tissue, passing the reference beam through a reference path having a path length which is adjustable to duplicate in the reference path the travel time of unscattered photons reflected from the sample tissue, recombining the reference beam and collected photons to form an interference pattern.

13. A method as described in claim 12, further comprising scanning the sample beam over the surface of the tissue to be characterized to produce a series of interference patterns.

14. A method for characterizing dental caries and periodontal disease in dental or periodontal tissue using optical imaging, comprising:

directing non-ionizing radiation of a selected wavelength onto a surface of the dental or periodontal tissue, wherein the wavelength simultaneously maximizes the number of photons reflected from tissue boundaries and minimizes the absorption of photons by the sample tissue.

collecting photons reflected by internal structures or interfaces of the tissue, discriminating between photon that are unscattered by the dental or periodontal tissue, and photons that are scattered by the tissue, based on the coherence of the reflected photons, selecting photons that are unscattered by the dental or periodontal tissue, interpreting the distribution of the selected photons to determine the characteristics of the dental or periodontal tissue.

15. A method for characterizing dental caries using optical imaging, comprising:
- directing non-ionizing radiation of a selected wavelength onto dental tissue,
- collecting photons transmitted through the dental tissue,
- discriminating between photons that are unscattered by the dental tissue, and photons that are scattered by the dental tissue, based on the coherence of the transmitted photons,
- selecting transmitted photons that-are unscattered by the dental tissue,
- interpreting the distribution of the selected photons to determine the presence and characteristics of dental caries.

16. A method as described in claim 15, wherein the wavelength of the non-ionizing radiation is in the wavelength region 500 nm to 1400 nm.

17. A method as described in claim 15, wherein the wavelength of the non-ionizing radiation is chosen to simultaneously maximize the differential absorption/scattering between carious and healthy dental tissue and the number of photons transmitted through the dental tissue.

18. A method as described in claim 15, wherein the transmitted photons are collected on an optical receiver to form an image.

19. A method as described in claim 10, wherein the optical receiver is a photodetector, a two-dimensional photodetector array, or photographic film.

20. A method as described in claim 15, wherein the non-ionizing radiation is generated by a source selected from the group consisting of continuous wave low coherence sources and highly coherent sources.

21. A method as described in claim 20, wherein the source is a continuous wave low coherence source selected from the group consisting of superluminescent diodes, diode-pumped solid state crystal sources, and diode-pumped rare earth-doped fiber sources.

22. A method as described in claim 21, wherein the discrimination between scattered and unscattered photons is accomplished by:
- splitting the incident beam of non-ionizing radiation into an incident sample beam and a reference beam,
- focusing the incident sample beam on one side of the tooth,
- collecting photons transmitted through the dental tissue,
- passing the reference beam through a reference path having a path length which is adjustable to duplicate in the reference path the coherence length of photons in the incident sample beam,
- recombining the reference beam and collected photons to form an interference pattern.

23. A method as described in claim 22, wherein the interpretation is accomplished by digitally reconstructing the interference pattern.

24. A method as described in claim 22, further comprising scanning the sample beam over the surface of the tooth to produce a series of interference patterns.

25. A method as described in claim 20, wherein the source is a highly coherent source selected from the group consisting of mode-locked diode lasers, diode-pumped mode-locked solid-state laser crystal sources, and diode-pumped mode-locked rare earth-doped fiber laser sources.

26. A method as described in claim 25, further comprising pulsing the source to emit pulses of non-ionizing radiation of the selected wavelength of pulse length $10^{-10}$ to $10^{-14}$ seconds.

27. A method as described in claim 26, wherein the discrimination is accomplished by:
- splitting the incident non-ionizing radiation into two beams,
- focusing the sample beam on one side surface of a tooth,
- collecting photons transmitted through the dental tissue,
- passing the reference beam through a reference path having a path length which is adjustable to duplicate in the reference path the transmission time of unscattered photons through the dental tissue,
- recombining the reference beam and collected photons to form an interference pattern.

28. A method as described in claim 27, further comprising scanning the sample beam over the surface of the tooth to produce a series of interference patterns.

29. A method for detecting dental caries using optical imaging, comprising:
- generating a series of 2-dimensional optical images of dental tissue at selected depths within the tooth,
- reconstructing the optical images to form 2-dimensional shadowgrams of cross-sections of the tooth,
- locating carious tissue by identifying the regions of lower reflection/higher absorption on the shadowgrams.

30. A method for establishing a diagnosis of gingivitis using optical imaging, comprising:
- generating a series of optical images of dental and periodontal tissue to locate tissue interfaces at various points along a vertical line down the side of a tooth and adjacent epithelium,
- determining from tissue interface data the location of the cemento-enamel junction, epithelial and connective tissue attachment levels, and alveolar bone level,
- calculating the depth of the periodontal pocket,
- comparing the results of the calculation of periodontal pocket depth and the bone and connective tissue attachment levels with medical criteria for gingivitis.

* * * * *